United States Patent [19]
Kamiya et al.

[11] Patent Number: 6,057,437
[45] Date of Patent: May 2, 2000

[54] ANTISENSE NUCLEIC ACID COMPOUNDS INHIBITING VASCULAR ENDOTHELIAL GROWTH FACTOR

[75] Inventors: Kinya Kamiya; Yoko Matsuda; Kiyoshi Uchida, all of Ibaraki, Japan

[73] Assignee: Taogosei Co. Ltd., Tokyo, Japan

[21] Appl. No.: 09/120,853

[22] Filed: Jul. 21, 1998

[30] Foreign Application Priority Data

Jul. 25, 1997 [JP] Japan ................................. 9-213838

[51] Int. Cl.[7] ........................ C07H 21/04; C12N 15/11; C12N 15/85; A61K 48/00
[52] U.S. Cl. ...................... 536/24.5; 536/231; 536/24.3; 536/24.31; 435/325; 435/366; 435/375; 514/44
[58] Field of Search .............................. 435/6, 69.1, 91.1, 435/440, 325, 366, 371, 375, 320.1; 536/23.1, 24.3, 24.31, 24.33, 24.5; 514/44

[56] References Cited

U.S. PATENT DOCUMENTS 5,639,736  6/1997  Robinson ................................. 514/44
5,639,872  6/1997  Robinson ............................... 536/24.5

FOREIGN PATENT DOCUMENTS

WO95/04142  9/1995  WIPO .
WO96/27006  6/1996  WIPO .

OTHER PUBLICATIONS

Crooke, S.T. Chapter 1 in "Antisense Research and Application", Stanley T. Crooke, ed., pp. 1–50 (Springer–Verlag, New York, 1998).

Branch, A.D. TIBS. Feb. 1998, vol. 23, pp. 45–50.

Gewirtz, A.M. et al. Proc. Natl. Acad. Sci. USA. Apr. 1996, vol. 93, pp. 3161–3163, Apr. 1998.

Rojanasakul, Y. Advanced Drug Delivery Reviews. Jan. 1996, vol. 18, pp. 115–131.

*Primary Examiner*—John S. Brusca
*Assistant Examiner*—Mark L. Shibuya
*Attorney, Agent, or Firm*—Fish & Richardson P.C.

[57] ABSTRACT

The present invention provides an antisense nucleic acid compound inhibiting expression of vascular endothelial growth factor as well as therapeutic and diagnostic agents comprising the same as an active ingredient. A compound which nucleotide sequence is substantially complementary to a nucleotide sequence located upstream of a translation region in a gene coding for vascular endothelial growth factor and which inhibits 50% or more of the expression of vascular endothelial growth factor in cells is used as the antisense nucleic acid.

17 Claims, 5 Drawing Sheets

FIG. 6

ANTISENSE NUCLEIC ACID COMPOUNDS INHIBITING VASCULAR ENDOTHELIAL GROWTH FACTOR

FIELD OF THE INVENTION

This invention relates to an antisense nucleic acid compound which contains a nucleotide sequence complementary to a specific nucleotide sequence in an untranslated region located 5'-upstream of a translation region in a gene coding for vascular endothelial growth factor and which inhibits the expression of vascular endothelial growth factor as well as to uses thereof, and this invention is directed to genetic technology, in particular pharmaceutical manufacturing and diagnostic drug technology.

BACKGROUND OF THE INVENTION

Extensive research has conventionally been made of tumors and tumor cells as a basis of development in an anticancer drug. As a result, it was found that solid tumors need oxygen and nutrients supplied through blood vessels for maintaining their homeostasis in vivo, and without such blood vessels, they cannot be grown to 2 mm or more in diameter in vivo [Basic Science of Cancer, authored by I. F. Tannock and R. P. Hill and translated by Naoyuki Taniguchi, Medical Science International (1993); and "Hatsugan to Gan Saibo" (Carcinogenesis and Cancer Cells)], Cancer Bioscience 3, edited by Toshio Kuroki, Tokyo University Press (1991)).

For this extension of blood vessels to solid tumors, it was proposed that solid tumor cells produce and secrete a certain factor (a tumor angiogenic factor) to induce blood vessels (J. Folkman, Annals of Surgery, Vol. 175, pp. 409–416 (1972)).

Attention has been paid to vascular endothelial growth factor as one of substances which functions as a tumor angiogenic factor (N. Ferrara et al., Endocrine Reviews, Vol. 3, No. 1, pp. 18–31 (1992)). Vascular endothelial growth factor is the same substance as so-called "vascular permeability factor", and in some cases it is also called "vascular endothelial growth factor/vascular permeability factor". As such factor, 4 kinds of molecular species, which occur due to the difference of splicing, are found in human.

Recently, it has been found that this vascular endothelial growth factor does not exert direct action (e.g. growth promotion) on solid tumor cells in experiments with cells (in vitro). However, it has been found that this factor promotes the growth of solid tumors in experiments with animals (in vivo). It has been further revealed that the growth of solid tumors is inhibited by administration of an anti-VEGF antibody to animals. These findings indicate that vascular endothelial growth factor is a tumor angiogenic factor (K. J. Kim et al., Nature, Vol. 362, April 29 issue, pp. 841–844 (1993); S. Kondo et al., Biochemical and Biophysical Research Communications, Vol. 194, No. 3, pp. 1234–1241 (1933)).

From the foregoing, inhibition of vascular endothelial growth factor leads to inhibition of growth of solid tumor cells, and this should be applicable in the development of anticancer agents. In fact there is a report on a method to use an anti-VEGF antibody. In this prior method, function of vascular endothelial growth factor (i.e. function of facilitating the growth of solid tumors) biosynthesized via translation of mRNA is inhibited by the anti-VEGF antibody.

However, this prior method is based on the assumption that vascular endothelial growth factor is present, therefore it is required for said factor not necessary to depress growth of tumor to be produced. Hence, this method cannot be effective until such substance is produced. Further, because vascular endothelial growth factor itself is biosynthesized without special inhibition, this method is problematic if the specificity and binding ability of the anti-VEGF antibody is poor and the inhibitory action of the antibody is incomplete.

Under these circumstances, there is proposed a method (referred to as antisense nucleic acid method) of using a nucleic acid compound (i.e. an antisense nucleic acid compound) which completely or almost completely inhibits expression of vascular endothelial growth factor itself by inhibiting production of vascular endothelial growth factors at the translation of mRNA, in place of inhibiting the action of vascular endothelial growth factor by use of said anti-VEGF antibody (Uchida et al., Antisense Res. & Dev., Vol. 5, No. 1, pp. 87–88, 1995; Nomura et al., J. Biol. Chem., Vol. 270, No. 47, pp. 28316–28324, 1995; WO 95/04142; WO 96/00286; WO 96/23065; WO 96/27006).

Whether the antisense nucleic acid method is effective or not depends on the method of selecting the antisense nucleic acid. That is, the method depends on how an effective nucleic acid compound completely or almost completely inhibiting production of vascular endothelial growth factor can be selected as the antisense nucleic acid compound. The present inventors have previously found and proposed antisense nucleic acid compounds which have nucleotide sequences complementary to the nucleotide sequence of the gene coding for vascular endothelial growth factor and which inhibit expression of vascular endothelial growth factor (International Publication WO 96/00286).

SUMMARY OF THE INVENTION

The present inventors have conducted studies with the aim of finding an antisense nucleic acid compound for inhibiting production of vascular endothelial growth factor more effectively than those previously proposed.

As a result of their eager study with this aim, the present inventors found that an antisense nucleic acid compound having a nucleotide sequence complementary to a nucleotide sequence located upstream of a translation region in a gene coding for vascular endothelial growth factor inhibits production of vascular endothelial growth factor more effectively than the previously proposed nucleic acid compounds, and the present inventors confirmed its pharmacological effect in a cultured cell system to complete the present invention.

That is, the present invention relates to an antisense nucleic acid compound which nucleotide sequence is substantially complementary to a nucleotide sequence located upstream of a translation region in a gene coding for vascular endothelial growth factor and which inhibits 50% or more of the expression of vascular endothelial growth factor in cells, and further to a therapeutic agent and diagnostic agent comprising said antisense nucleic acid compound as an active ingredient.

DETAILED DESCRIPTION OF THE INVENTION

Hereinafter, the present invention is described in detail.

The phrase "nucleotide sequence located upstream of a translation region in a gene coding for vascular endothelial growth factor" herein used means a nucleotide sequence (including a promoter, an operator etc.) located upstream of a structural gene defining the amino acid sequence of vascular endothelial growth factor, and an example is shown in SEQ ID NO:1.

The phrase "inhibit the expression of vascular endothelial growth factor" herein used means that production of vascular endothelial growth factor is inhibited or prevented by inhibiting e.g. translation of mRNA encoding vascular endothelial growth factor.

Preferable antisense nucleic acid compounds are those inhibiting expression of vascular endothelial growth factor effectively, and according to the present invention, antisense nucleic acid compounds having nucleotide sequences complementary to at least 10, preferably 13, more preferably 20 contiguous nucleotides in the nucleotide sequences of SEQ ID NOS:2 to 19, which are located upstream of a translation region in vascular endothelial growth factor gene shown in SEQ ID NO:1, inhibit the expression of vascular endothelial growth factor at a level of 50% or more, generally 70% or more, and in some cases 80% or 90% or more as compared to the expression in the absence of the compounds, and it can be said that they are significantly superior antisense nucleic acid compounds. The effect of these antisense nucleic acid compounds was confirmed by using a cultured cell system described below.

The antisense nucleic acid compounds of the invention are obtained in the following manner by designing nucleic acid compounds on the basis of the idea of the antisense nucleic acid method and evaluating their effect on production of vascular endothelial growth factor on the basis of the amount of the protein of said factor produced.

That is, nucleotide sequences upstream of a translation region in the gene coding for vascular endothelial growth factor (referred to hereinafter as "VEGF") are examined. Then, nucleic acid compounds complementary to said nucleotide sequences are prepared by chemical synthesis etc.

Then, the inhibitory effect of said compounds on production of VEGF is confirmed by using a cultured cell system. That is, cells producing VEGF are cultured in the presence of said nucleic acid compounds to examine whether production of VEGF in said cultured cells is inhibited or not, and nucleic acid compounds inhibiting production of VEGF are regarded as antisense nucleic acid compounds.

In the present invention, if a synthetic nucleic acid compound inhibits expression of VEGF at higher degrees than by a nucleic acid compound having a random nucleotide sequence, said synthetic compound was regarded as antisense nucleic acid compound significantly inhibiting the expression. The "random nucleotide sequence" refers to a nucleotide sequence having not more than statistically expected degrees of complementation.

(1) Synthesis of Nucleic Acid Compound

The energy for forming a double-stranded chain of nucleotides is calculated, and from prediction of the secondary structure of VEGF mRNA (Naoki Sugimoto, Biophysics, Vol. 33, No. 2, pp. 1–8, Journal of Japanese Biophysical Society, 1993) and target-site prediction, a nucleotide sequence consisting of 10 to 30 nucleotides is selected from nucleotide sequences in a region presumed to elicit the antisense nucleic acid effect, e.g. a region presumed not to form a double-stranded chain in such as VEGF mRNA, and a nucleic acid compound complementary to said nucleotide sequence is prepared by synthesis. Alternatively, nucleic acid compounds complementary to nucleotide sequences each consisting of 10 to 30 contiguous nucleotides whose positions are 1 to 10 nucleotides apart from one other in the whole region of the nucleotide sequence coding for VEGF are prepared by synthesis.

However, the latter method needs much time, cost and human investments, resulting in a poor efficiency. Accordingly, it is preferred that the former calculation etc. are used to limit a region presumed to have the effect and its effect is experimentally confirmed.

The nucleic acid compounds include natural form of oligodeoxyribonucleotides, phosphorothioate form of oligodeoxyribonucleotides, phosphorodithioate form of oligodeoxyribonucleotides, methylphosphonate form of oligodeoxyribonucleotides, phosphoramidate form of oligodeoxyribonucleotides, H-phosphonate form of oligodeoxyribonucleotides, triester form of oligodeoxyribonucleotides, α-anomer form of oligodeoxyribonucleotides, those oligoribonucleotide which correspond to said oligodeoxy-ribonucleotides, peptide nucleic acids, chimera form of oligomers thereof, other artificial nucleic acids, and nucleic acid-modified compounds. Among these, the natural form and phosphorothioate form of oligodeoxyribonucleotides are preferable because of their less nonspecific inhibition of expression, easiness of their synthesis etc. and because their hybrid (double-stranded chain) with mRNA can act as a substrate for RNase H.

The synthesis of the natural form of nucleic compound can be carried out with e.g. a 381A DNA synthesizer or 394 DNA/RNA synthesizer manufactured by ABI (Applied Biosystems Inc.) in accordance with the phosphoramidite method (see instructions available from ABI, or F. Eckstein, Oligonucleotides and Analogues: A Practical Approach, IRL Press (1991)). Further, they can also be synthesized in a similar manner using an Expedite DNA/RNA synthesizer (PerSeptive Biosystems) or Gene Assembler (Pharmacia Biotec).

In the phosphoramidite method, a nucleic acid-related compound is synthesized by condensing the 3'-terminal of a modified deoxyribonucleoside or modified ribonucleoside to the 5'-terminal of another modified deoxyribonucleoside, modified ribonucleoside, oligo-modified deoxyribonucleotide or oligo-modified-ribonucleotide by use of a reagent containing phosphoramidite protected with a cyanoethyl group etc.

The final cycle of this synthesis is finished to give a product with a protective group (dimethoxytrityl group etc.) bound to a hydroxyl group at the 5'-terminal of the sugar moiety. The oligomer thus synthesized at room temperature is cleaved off from the support, and its nucleotide and phosphate moieties are deprotected. In this manner, the natural form of oligonucleic acid compound is obtained in a crude form.

The phosphorothioate form of nucleic acid compound can also be synthesized in a similar manner to the above natural form by the phosphoramidite method with the aforesaid synthesizer. Synthesis in this case is feasible by replacing the oxidation step by a sulfurization step using a sulfurization reagent during the synthetic cycle in the phosphoroamidite method. The procedure after the final cycle of the synthesis is also the same as with the natural form.

To inhibit expression of the gene, the nucleic acid compound should be a nucleic acid compound having a nucleotide sequence complementary to 10 or more contiguous nucleotides, preferably 13 or more contiguous nucleotides, more preferably 20 or more contiguous nucleotides as previously revealed by the present inventors, and the number of nucleotides is not limited within the ranges herein described. Although a nucleotide sequence complementary to 30 or more nucleotides may be used, no further improvement can be achieved and it is difficult to synthesize such a long sequence, therefore the nucleic acid compound having a nucleotide sequence complementary to 30 or less nucleotides which suffices to achieve the object of the present invention is synthesized as the target compound.

The crude nucleic acid compound thus obtained can be purified in a usual manner e.g. ethanol precipitation, or reversed phase chromatography, ion-exchange chromatography and gel filtration chromatography in high performance liquid chromatography (HPLC), supercritical fluid chromatography, and it may be further purified by electrophoresis. A cartridge for reversed phase chromatography (e.g. tC18-packed SepPak Plus; Waters) can also be used.

The purification of the phosphorothioate form of nucleic acid compound (20-mer, about 3 mg compound in a crude form) is carried out in a similar manner to the above natural form.

The purity of the natural form and phosphorothioate form of nucleic acid compounds can be analyzed by HPLC, capillary gel electrophoresis etc.

The synthesized nucleic acid compounds are used for screening test as described below.

(2) Antisense Nucleic Acid Effect in a Cultured Cell System

A pharmacological test to show that the antisense nucleic acid compound of the invention is useful as a therapeutic or diagnostic agent is carried out in which the nucleic acid compound synthesized in (1) above is added solely or with reagent facilitating incorporation of antisense nucleic acid compound into cells, to cultured cells expressing VEGF, in order to examine its inhibition of VEGF expression.

That is, the antisense nucleic acid compound such as natural form of oligodeoxyribonucleotide or phosphorothioate form of oligodeoxyribonucleotide is added at a concentration of 0.01 to 100 $\mu$M, preferably 0.1 to 10 $\mu$M, to cells derived from mammals such as human, mouse, rat, guinea pig, bovine etc. under germ-free conditions, if necessary in the presence of reagents facilitating incorporation of antisense nucleic acid compound into cells, such as Lipofectin reagent, Lipofectamine reagent, DOTAP reagent, artificial synthetic lipid vehicle, liposome, membrane fusion reagent, polymeric micellar reagent, polymeric carrier, Tfx reagent etc. The inhibition of the target protein (VEGF) expression can then be evaluated by e.g. ELISA (enzyme-linked immunosorbent assay) or Western blotting using anti-VEGF antibody to confirm the inhibitory effect of the antisense nucleic acid compound on the expression of the protein.

To confirm the formation of VEGF in the above-described cultured cell system, the following two methods may be used.

The first method is sandwich form of enzyme linked immunoassays (see e.g. E. Harlow, D. Lane, Antibodies: A Laboratory Manual, Cold Spring Harbor Laboratory (1988)) using anti-VEGF polyclonal antibodies [antibodies obtained from a rabbit previously administered with human-derived VEGF as a product of E. coli (see S. Kondo et al., Biochemical and Biophysical Research Communications, Vol. 194, No. 3, pp. 1234–1241 (1993))].

This is a generally well-known method and carried out specifically as follows:

The above-described anti-VEGF polyclonal antibodies are immobilized onto a microtiter plate in a usual manner (see e.g. Antibodies: A Laboratory Manual supra). Then, a reaction mixture in which the above-described cultured cells expressing VEGF were maintained at a suitable temperature for a suitable period is put to each well of the microtiter plate. The plate was left at room temperature and then washed. Thereafter, the above-described anti-VEGF polyclonal antibodies previously labeled with horseradish peroxidase are put to each well, left at room temperature, and washed. An ortho-diaminobenzene solution is added thereto as substrate and left at room temperature until suitable coloration takes place. The absorbance of the solution is determined to evaluate the content of VEGF.

The second method is the Western blotting method in which formation of VEGF in the above-described cultured cell system is confirmed by conducting SDS-PAGE (sodium dodecyl sulfate-polyacrylamide gel electrophoresis), then transferring an image of the protein onto a membrane, reacting the target protein with the labeled antibody and confirming it by autoradiography.

The Western blotting method can be conducted in a usual manner (e.g. Protein Experiment Protocol edited by Shigeo Ohono, et al. and published by Shujun K.K., 1997) and a typical example is as follows:

The protein is denatured by adding SDS sample buffer to a culture medium of cultured cells. This sample is added to each well of sodium dodecyl sulfate-polyacrylamide gel provided in an electrophoresis chamber and then electrophoresed by SDS-PAGE (15% or 17.5% polyacrylamide gel) while its high-order structure is maintained. Then, the gel after electrophoresis is overlaid on a nitrocellulose membrane, a nylon membrane or the like, and the electrophoresis image is transferred (blotted) onto the membrane in a blotting apparatus etc. To prevent unspecific reaction, this membrane has previously been blocked with 5% skimmed milk etc. Then, it is brought into contact with solution of VEGF antibody labeled with a radioisotope e.g. $^{125}$I so that the VEGF transferred onto the membrane is bound specifically to the VEGF antibody. The non-specifically adsorbed VEGF antibody is removed by washing, and autoradiography is then conducted. That is, the gel and an X-ray film are put together into a cassette in the dark. After this cassette is left at room temperature for several hours to dozens of hours, the X-ray film is developed. If VEGF has been expressed, a band appears at a position corresponding to the molecular weight of VEGF. If the expression of VEGF has been inhibited by the antisense nucleic acid compound, said band does not appear or weakly appears.

The inhibitory effect of the added nucleic acid compound, that is, the antisense nucleic acid compound, on VEGF expression can be evaluated by comparing with expression in the absence of the compound. For example, VEGF produced is quantified by the sandwich enzyme immunoassays or the Western blotting method as described in the method of confirming whether VEGF is formed or not, and the resulting density by autoradiography may be quantified with a densitometer. Formation of VEGF can be confirmed by comparing its quantified amount in the presence of the antisense nucleic acid compound with its quantified amount in the absence of the compound.

This quantified amount should be corrected using the number of cells per cell culture unit for the following 2 reasons.

One reason is an error in weighing. For example, let us assume that a predetermined volume of a cell suspension is added to each well of a culture plate to initiate incubation. When a suspension is obtained, weighing error occurs. This weighing error results from difficulty in reproducibly and repeatedly obtaining a predetermined amount of the sample or from heterogeneity of the cell suspension.

Another reason is a possible toxicity of samples and reagents added to cells. For example, some partial sequences of nucleic acid compounds are known to have specific inhibitory action on protein (see e.g. Arthur M. Krieg et al., Antisense & Nucleic Acid Drug Development, Vol. 7, pp. 115–123, 1997; C. A. Stein et al., Science, Vol. 261, pp. 1004–1012, 1993), by which a reduction in the number of cells can occur.

For these reasons, there are cases where the amount of VEGF expressed per cell culture unit cannot be used for accurate comparison. Accordingly, its correction by the number of living cells per cell culture unit is necessary for accurate comparison of the amount of VEGF expressed.

For example, there are the following 2 methods to find the number of living cells in the above-described cultured cell system. The first method is a classical cell counting method to determine the number of cells by using microscopes. In this method, to a cell-containing solution is added an about 1/25 volume of 0.5% trypan blue. Because dead cells are stained with trypan blue but living cells are not, only living cells can be counted under a microscope.

The second method is an MTT method utilizing a biological reaction in living cells. It is known that MTT (3-(4,5-dimethylthiazol-2-yl)-2,5-diphenyltetrazolium bromide, water-soluble, yellow) acts selectively on mitochondria of living cells, particularly on their respiratory chain, and MTT is cleaved to form MTT formazan (water-insoluble, purple).

When cells are treated with an MTT-containing medium, the amount of MTT formazan produced after a certain period is proportional to the number of living cells and can thus be used to determine the number of living cells (see, for example, Masato Nishida, et al., Human Cell, Vol. 5, No. 1, pp. 87–98, 1992; J. Carmichael et al., Cancer Research, Vol. 47, pp. 936–942, 1987).

Taking into amount of correction of the number of living cells, inhibition of gene expression can be estimated.

An antisense nucleic acid compound thus obtained is useful as a therapeutic agent to inhibit the growth of solid tumor cells or treat rheumatoid arthritis and diabetic retinopathy, or as a diagnostic agent for cancers and other diseases.

When the antisense nucleic acid compound of the present invention is used as a therapeutic agent, its target is not particularly limited. For example, the object of administration may be to prevent or treat various kinds of cancer. The compound may be administered orally or parenterally. The oral administration includes sublingual administration. The parenteral administration includes injection (e.g. subcutaneous, intramuscular, intravenous, intra-arterial injection or infusion), suppository, ointment, poultice etc. The dose can be varied within a wide range depending on whether compound is administered to animal or human, or on the age, administration route or intervals of administration. An effective amount of the antisense nucleic acid compound of the invention or an effective amount of the antisense nucleic acid compound used with a suitable diluent or with a pharmacologically acceptable carrier ranges from 1 to 100,000 μg/kg body weight/day, and is administered successively or once or in portions every day.

Tablets, granules, powder, capsules etc., in the case of oral administration of the antisense nucleic acid compound of the invention, contain customary additives such as binders, fillers, lubricants, disintegrator, wetting agent etc. Liquid preparations for oral administration may be in the form of oral aqueous agent, suspension, emulsion, syrup etc. It is also possible to use a dried product to be dissolved before use. The composition may further contain any additives and preservatives. In the case of parenteral administration, the preparation contains additives such as stabilizer, buffer, preservative, isotonic agent etc., usually in an ampoule for single administration, a vessel for multiple administrations or in a tube. The composition may be powder to be dissolved in suitable liquid e.g. pyrogen-free sterilized water.

The antisense nucleic acid compound of the invention can be used as a diagnostic agent e.g. in the following case.

Because it is known that cancer cells generally produce VEGF, cancer cells can be diagnosed by examining the amount of VEGF expression in cells with a probe of the nucleic acid compound invented with a nucleotide sequence complementary to a specific nucleotide sequence in the VEGF-coding gene or its transcribed mRNA.

According to the present invention, there is provided an antisense nucleic acid compound inhibiting the expression of the gene coding for VEGF.

The antisense nucleic acid compound of the present invention can inhibit the growth of solid tumors by inhibiting the expression of VEGF i.e. a factor facilitating the arrival of blood vessels at the solid tumors. Therefore, it can be used as an anticancer drug to inhibit the growth of solid tumor cells. Because VEGF is involved in rheumatoid arthritis and diabetic retinopathy, the antisense nucleic acid compound of the present invention can also be used as a therapeutic agent for such diseases.

Further, the antisense nucleic acid compound of the present invention can be used as a diagnostic agent for detection of solid tumor cells as well as for diagnosis of rheumatoid arthritis and diabetic retinopathy.

EXAMPLES

Hereinafter, the present invention is described in more detail with reference to the Examples which however are not intended to limit the scope of the present invention.

Example 1

Synthesis and Purification of Phosphorothioate Form of Nucleic Acid Compound

The purification of the phosphorothioate form of nucleic acid compounds (20-mer, about 3 mg in a crude form) was carried out in the following manner.

Phosphorothioate form of nucleic acid compounds (20-mer) having a complementary sequence to the nucleotide sequence of SEQ ID NO:1 or with a random sequence were synthesized with a 381A DNA synthesizer or 394 DNA/RNA synthesizer manufactured by ABI (ABI Biosystems Inc.) by the phosphoramidite method in accordance with the manufacture's instructions. They are 18 nucleotides shown in Table 1, i.e. U0370TS to U0865TS. The final cycle of this synthesis was finished to give a product with a protective group (dimethoxytrityl group) bound to the 5'-terminal hydroxyl group of its sugar moiety. At room temperature, the synthesized oligomer was cleaved off from the support by treatment with about 30% ammonium water for 60 minutes. The product was kept at 55° C. for 8 hours to deprotect its base and phosphate moieties.

The crude phosphorothioate form of oligodeoxyribo-nucleotide thus obtained was purified by reversed phase HPLC in the following manner.

A reversed phase HPLC column (μ-Bondasphere, C18, 300, 5μ, 150 mm length, available from Waters) was equilibrated with 5% acetonitrile-95% TEAA (TEAA: 0.1 M triethyl ammonium acetate, pH 7.2). The crude phosphorothioate form of oligodeoxyribonucleotide was applied to this column. The sample was eluted with a linear gradient of 2%/min. acetonitrile at 25° C. at a flow rate of 1 ml/min. The eluate was monitored at 260 nm, and the desired 20-mer compound with the protective group (dimethoxytrityl group) bound to the hydroxyl group at the 5'-terminal of the sugar moiety, which was eluted between 25 and 30 minutes after the start of the elution, was collected. The collected solution was dried under reduced pressure, and 40% acetic acid was added to and mixed with it, and the mixture was then stirred and left at room temperature, and the dimethoxytrityl group was eliminated from the 5'-terminal of the sugar moiety. After 1 hour, an equal volume of sterilized water was added and stirred, and 2-fold excess diethyl ether was further added and the mixture was vigorously stirred. The solution was left until it was separated into 2 layers, and the upper layer (ether layer containing the eliminated dimethoxytrityl group) was removed. This ether extraction was repeated 4 times. The extract was dried under vacuum, then 0.5 ml sterilized water was added thereto, and it was vigorously stirred. It was applied to a column packed with ion-exchanger Dawex-50 (Aldrich) through which sterilized water was then sufficiently passed. Subsequently, the phosphorothioate form of oligodeoxyribonucleotide was eluted with a gradient of 0.1 M/min. sodium chloride. The eluate was monitored at 260 nm and the desired product was collected. This product was adequately dialyzed for removal of excess sodium chloride.

Figure 1:
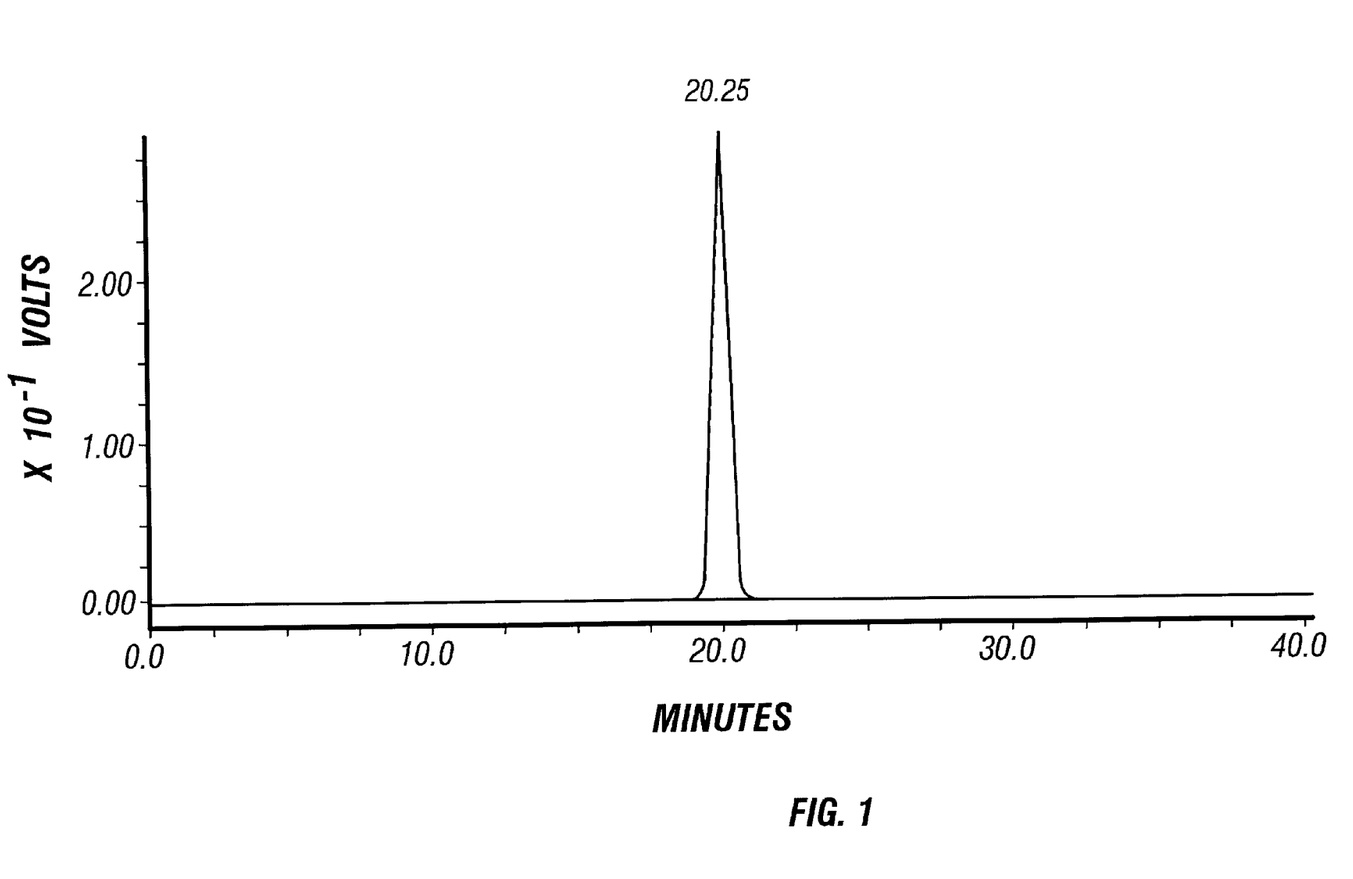
FIG. 1 shows an example of reversed phase HPLC analysis of a purified sample.
Figure 2:
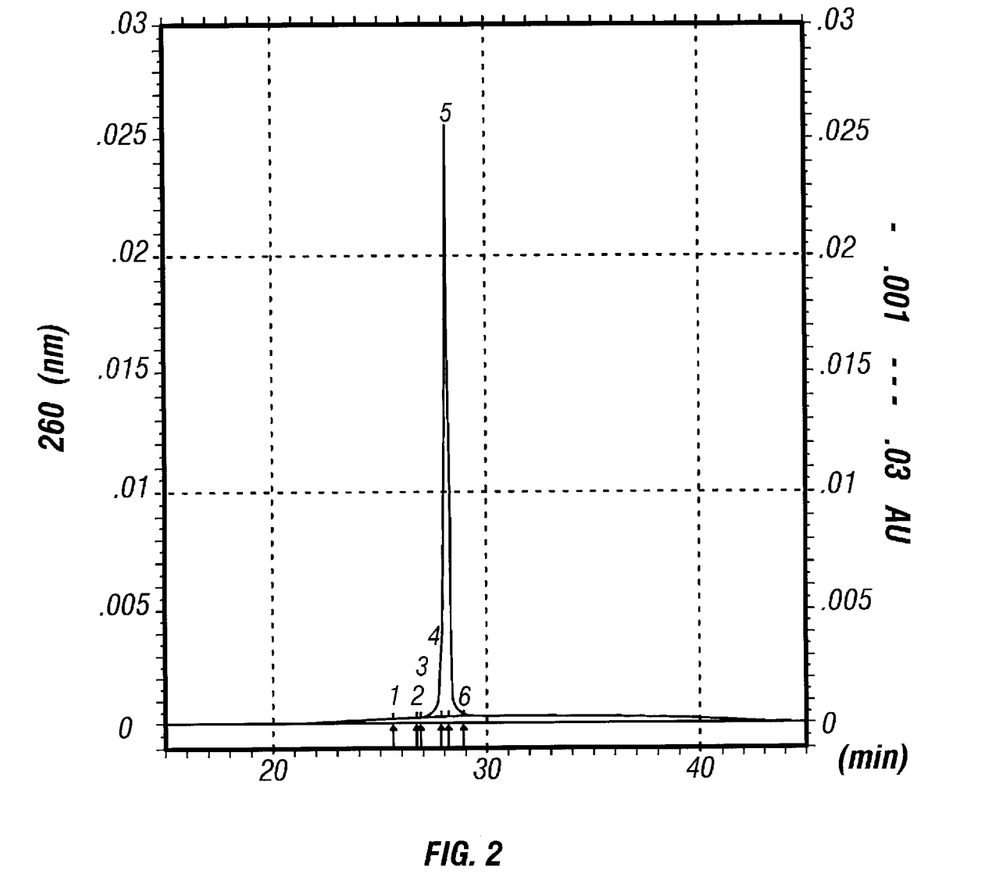
FIG. 2 shows an example of capillary gel electrophoresis of a purified sample.
Figure 3:
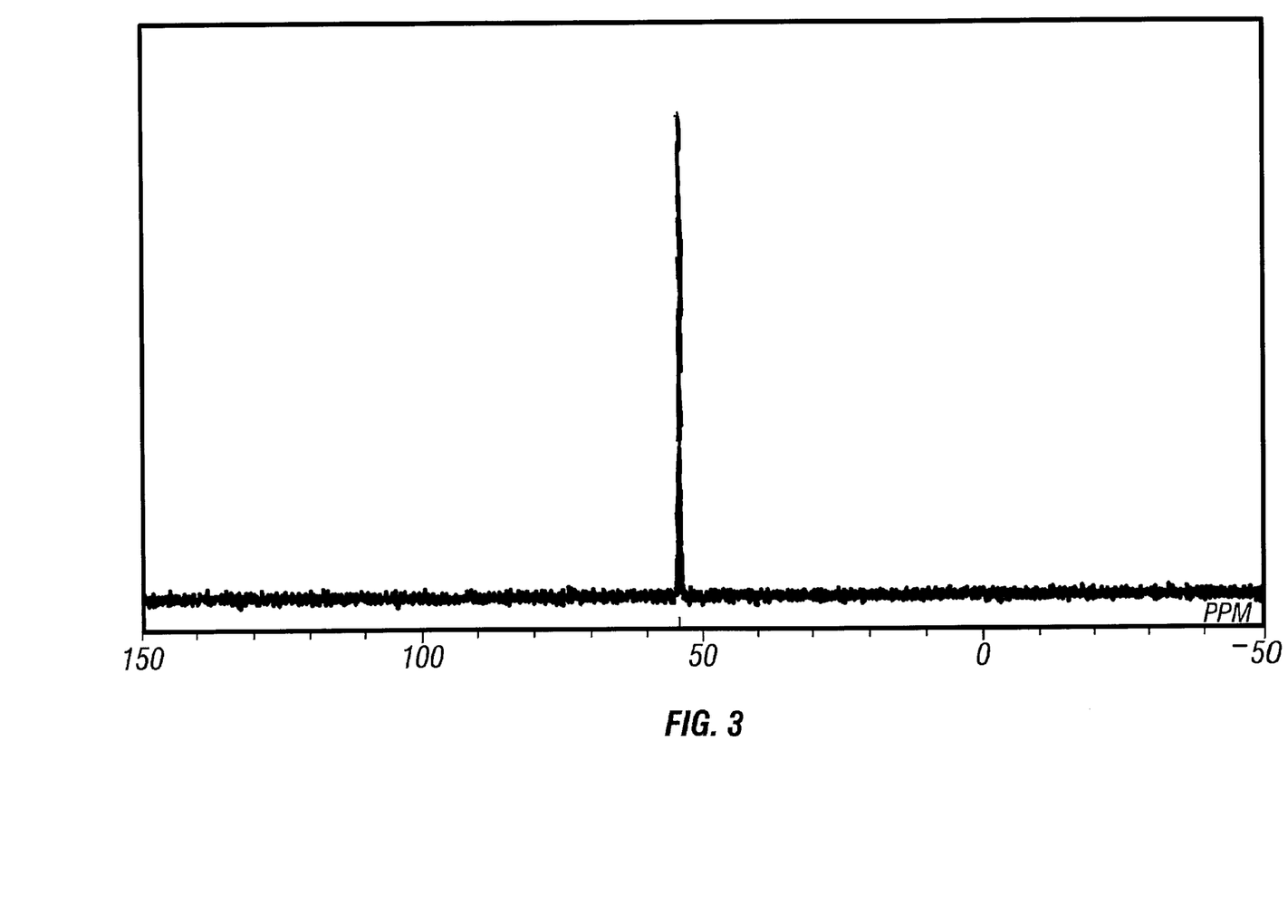
FIG. 3 shows an example of $^3$P-NMR spectrum of a purified sample.
Figure 4:
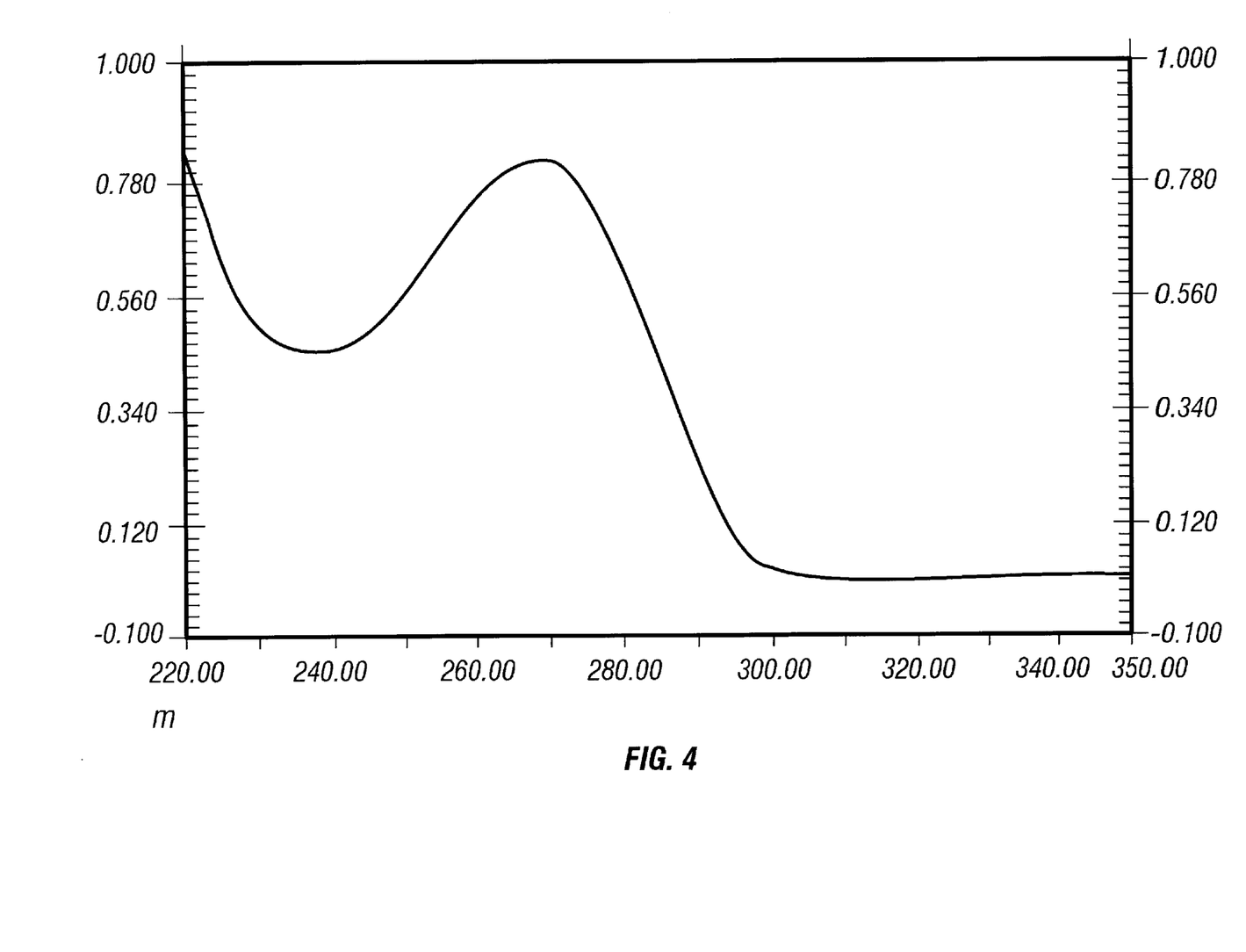
FIG. 4 shows an example of an UV absorption spectrum of a purified sample.

The purity of the phosphorothioate form of oligodeoxyribonucleotide thus obtained was examined by reversed phase HPLC, capillary gel electrophoresis, $^{31}$P-NMR and UV absorption spectroscopy. Their analysis conditions etc. are as follows:

(i) Reversed phase HPLC analysis
Column: μ-Bondasphere (C18, 300 Å, 5μ, 3.9×150 mm, purchased from Waters).
Buffer: Acetonitrile-100 mM triethyl ammonium acetate (pH 7.2).
Gradient elution: Acetonitrile 5%→85%/40 minutes, linear gradient.
Temperature: 25° C.
Detection wavelength: 260 nm.
A chromatogram for U0853TS is shown in FIG. 1.
(ii) Analysis by Capillary Gel Electrophoresis
Column: μPAGE (5% T, 5% C polyacrylamide gel, 7 M urea, 75 μm×55 cm, purchased from J & W).
Buffer: 100 mM Tris-borate buffer (pH 8.3), 7 M urea.
Voltage: 230 V/cm.
Temperature: room temperature.
Detection wavelength: 260 nm.
A chromatogram for U0853TS is shown in FIG. 2.
(iii) $^{31}$P-NMR Analysis
Measurement solvent: heavy water.
Resonance frequency: 162 MHz.
Temperature: room temperature.
External standard: trimethoxyphosphine (140.0 ppm).
A spectrum for U0853TS is shown in FIG. 3.
(iv) Analysis by UV Absorption Spectrum
Solvent: 20 mM sodium phosphate buffer and 100 mM NaCl, pH 7.0.
A spectrum for U0853TS is shown in FIG. 4.
FIGS. 1 to 3 show that the compound has adequate purity for use in the experiments of the present invention, and from FIG. 4, the UV absorption spectrum of the compound agrees with UV absorption spectrum of a nucleic acid compound.

The nucleotide sequences of the synthesized phosphorothioate form of deoxyribonucleotides are shown in Table 1.

In item "Sample #" in Table 1, the nucleotide sequences given "U" before their numbers are antisense chains, i.e. chains complementary to a sense chain upstream of a translation region coding for VEGF. The nucleotide sequences given "R" are random sequences. For example, "RU0406" is identical in nucleotide composition to "U0406", but is different in respect of randomly positioned nucleotides.

The specific sequence (20-mer) of each sample # is shown in item "Nucleotide sequence" in Table 1. The numbers in item "Complementary region in SEQ ID NO:1" indicate the nucleotide sequence region in SEQ ID NO:1 to which each oligodeoxyribonucleotide corresponds. For example, "U0370" is a 20-mer antisense nucleic acid compound composed of a complementary sequence to a nucleotide sequence consisting of nucleotides 308 to 327 in SEQ ID NO:1 in the Sequence Listing.

TABLE 1

Nucleotide sequences of synthesized antisense nucleic acids and their corresponding complementary regions in SEQ ID NO:1

| Sample # | Nucleotide sequence 5'← →3' | Complementary region in SEQ ID NO:1 | SEQ ID No. |
|---|---|---|---|
| U0370TS | ACCTCTTTCCTCTTTCTGCT | 308~327 | 4 |
| U0393TS | GACTTCTCTCTGGAGCTCTT | 331~350 | 5 |
| U0397TS | CCTCGACTTCTCTCTGGAGC | 335~354 | 6 |
| U0401TS | TCTTCCTCGACTTCTCTCTG | 339~358 | 7 |
| U0406TS | CTCTCTCTTCCTCGACTTCT | 344~363 | 8 |
| RU0406TS | TTCCTTCCCTTCTAGTCCTC | – | 20 |
| U0411TS | CCCGTCTCTCTCTTCCTCGA | 349~368 | 9 |
| U0413TS | ACCCCGTCTCTCTCTTCCTC | 351~370 | 10 |
| RU0413TS | CCCTCTCGTCTCCTACTCTC | – | 21 |
| U0416TS | CTGACCCCGTCTCTCTCTTC | 354~373 | 11 |
| U0420TS | CTCTCTGACCCCGTCTCTCT | 358~377 | 12 |
| U0424TS | CGCTCTCTCTGACCCCGTCT | 362~381 | 13 |
| U0843TS | TTCTCTTCTTCCTCCTCCCC | 781~800 | 14 |
| U0848TS | CTTCCTTCTCTTCTTCCTCC | 786~805 | 15 |
| U0853TS | CTCCTCTTCCTTCTCTTCTT | 791~810 | 16 |
| U0857TS | CCCTCTCCTCTTCCTTCTCT | 795~814 | 17 |
| U0860TS | GCCCCTCTCCTCTTCCTTC | 798~817 | 18 |
| U0865TS | CTGCGGCCCCTCTCCTCTT | 803~822 | 19 |

Example 2
Confirmation of Antisense Nucleic Acid Effect in HT1080 Cell System

The purified phosphorothioate form of oligodeoxyribonucleotide was dried again under vacuum, then diluted to a predetermined concentration, and evaluated for its effect on the expression of VEGF in a cultured cell system.

The concentration of the oligodeoxyribonucleotide was determined from the absorbance of the oligodeoxyribonucleotide in buffer, pH 7.0 (20 mM sodium phosphate and 100 mM NaCl) at 260 nm and 80° C. in a cuvette of 1 cm light path length by use of its molecular absorption coefficient determined by the nearest-neighbor approximation method on the basis of the reported molecular absorption coefficients of mononucleotide and dinucleotide (E. G. Richards, Handbook of Biochemistry and Molecular Biology: Nucleic Acids (edited by C. D. Fasman), 3rd ed., vol. I, p. 197, CRC Cleveland, Ohio).

The effect of antisense nucleic acid of the present invention on VEGF expression in the cultured cell system using human fibrosarcoma cells HT1080 was examined under sterilized conditions by the reported method (M. Y. Chiang et al., The Journal of Biological Chemistry, Vol. 266, No. 27, pp. 18162–18172 (1991)), as follows:

HT1080 cells were placed in a 48-well plate and incubated at 37° C. in a 5% $CO_2$ atmosphere in Dulbecco's modified Eagle medium (DMEM) containing 10% fetal bovine serum until they attained a 50 to 70% confluent state. After removal of the medium, the plate was washed with Opti-MEM medium (GIBCO-BRL). Tfx™-50 reagent (Promega) was put at a final concentration of 18 $\mu$g/ml to the Opti-MEM medium containing 2.3 $\mu$M phosphorothioate form of oligodeoxyribonucleotide, and the mixture was stirred. After the mixture was left for 15 to 20 minutes at room temperature, 0.2 ml was put to each well, and the plate was incubated at 37° C. for 4 hours in a 5% $CO_2$ atmosphere. The solution was removed, and the plate was washed with DMEM medium containing 10% fetal bovine serum. Then, 100 $\mu$l DMEM medium containing 10% fetal bovine serum was put to each well and the plate was incubated at 37° C. for 2 hours in a 5% $CO_2$ atmosphere.

The amount of VEGF in the medium was determined by enzyme immunoassays as described below, and the number of living cells was determined by a method of measuring the number of living cells as described below.

Enzyme Immunoassays

Anti-VEGF polyclonal antibodies (i.e. antibodies obtained from a rabbit given human-derived VEGF produced by E. coli) were immobilized in a usual manner onto a polystyrene microtiter plate. Then, 100 $\mu$l of the above-described cell culture (supernatant cultured at 37° C. for 2 or 3 hours) or 100 $\mu$l DMEM medium containing 10% fetal bovine serum and VEGF at various concentrations in the range of 50 to 1500 pg/ml were added to each well. The plate was left at room temperature (about 25° C.) for 2 hours. This solution was removed, and the plate was washed with a phosphate buffer containing 0.1% bovine serum albumin. Then, the above-described polyclonal antibodies labeled with horseradish peroxidase were added to each well and left at room temperature for 1 hour. The plate was washed sufficiently with the same phosphate buffer, and an orthodiaminobenzene solution was added thereto as oxidase substrate and left at room temperature until suitable coloration took place (about 30 minutes) Thereafter, its absorbances at 490 nm and 650 nm were determined, and the difference between these absorbances was calculated (absorbance at 490 nm–absorbance at 650 nm) to evaluate its VEGF content. The content was calculated using a standard curve obtained with standard samples on the same plate.

Method of Determining the Number of Living Cells (MTT Method)

A solution of 0.5 mg MTT in 1 ml DMEM medium containing 10% fetal bovine serum was used as MTT solution. The MTT solution was added in an amount of 200 $\mu$l/well to a 48-well plate from which the cell culture medium was removed, to determine the amount of VEGF expressed by enzyme immunoassays. The plate was incubated in a 5% $CO_2$ atmosphere at 37° C. for 2 hours. The cell culture medium was removed, and 200 $\mu$l DMSO (dimethylsulfoxide) was added to it. It was sufficiently stirred to make the solution uniform. Thereafter, its absorbances at 490 nm and 650 nm were determined, and the difference between these absorbances was calculated (absorbance at 490 nm–absorbance at 650 nm) and extrapolated to a calibration curve to determine the number of living cells.

The calibration curve was obtained from previously measured absorbance in the presence of predetermined numbers of cells.

Figure 5:
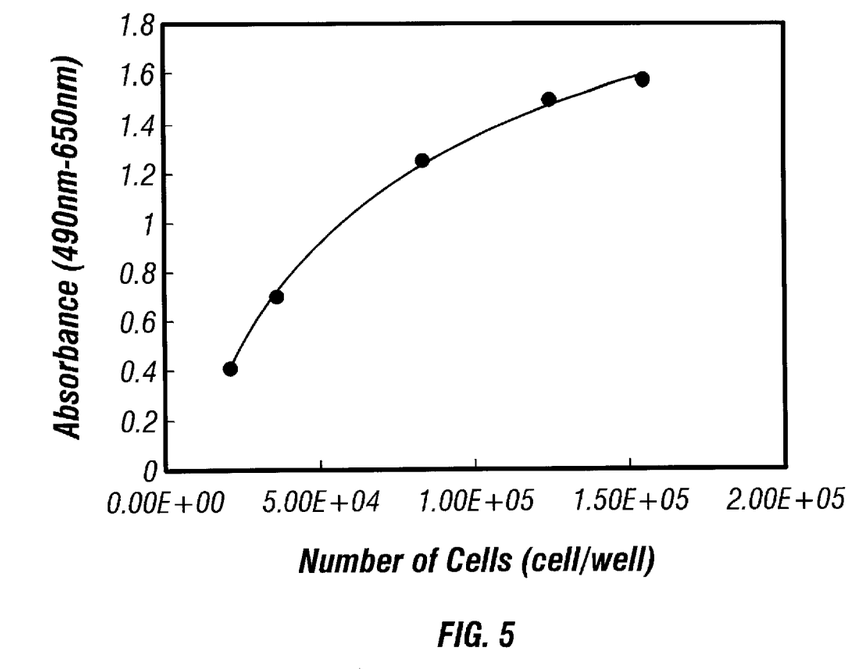
FIG. 5 shows a calibration curve used for the MTT method.

The calibration curve obtained in the case of HT1080 is shown in FIG. 5.

Figure 6:
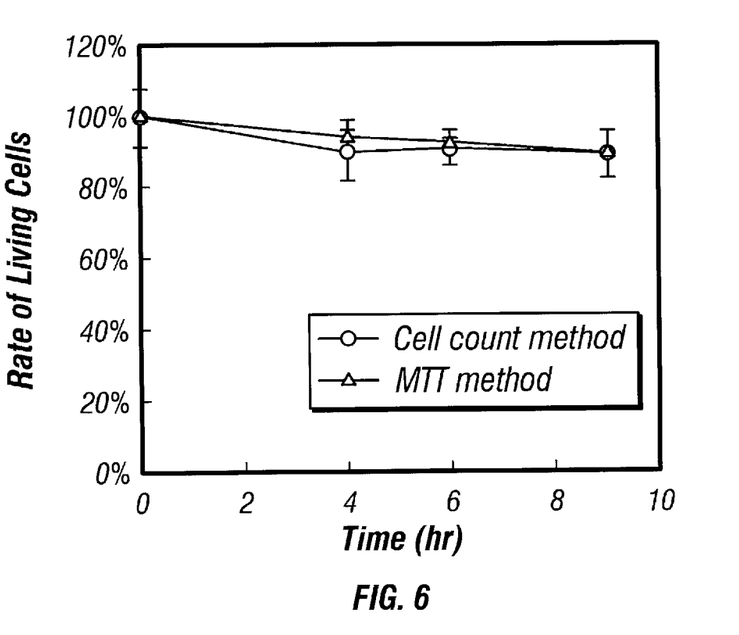
FIG. 6 shows a good correlation between the cell count method and the MTT method.

A good correlation between the number of cells counted and the absorbance obtained from the MTT method under the present experimental conditions was found as shown in the following experiment.

HT1080 cells were placed in a 48-well plate and incubated at 37° C. in DMEM medium containing 10% fetal bovine serum in a 5% $CO_2$ atmosphere until they attained a 50 to 80% confluent state. After removal of the medium, the plate was washed with Opti-MEM medium (GIBCO-BRL). HT1080 cells were incubated at 37° C. in a 5% $CO_2$ atmosphere for 2 or 4 hours in Opti-MEM medium containing 2.3 $\mu$M mixed sequences of phosphorothioate form of oligodeoxyribonucleotides (a mixture of $4^{20}$ kinds of 20-mer oligonucleotide synthesized such that A (adenine), G (guanine), C (cytidine), and T (thymidine) were present in theoretically equal amounts) and 18 $\mu$g/ml Tfx™-50 reagent. After removal of the Opti-MEM medium containing the reagent, the plate was washed with DMEM medium containing 10% fetal bovine serum. Thereafter, 200 $\mu$l DMEM medium containing 10% fetal bovine serum was added and the mixture was incubated at 37° C. in a 5% $CO_2$ atmosphere for a predetermined period. Then, the number of living cells was determined in the cell count method using a trypan blue solution (the number of cells was determined with a microscope). At the same time, the number of cells was determined by the MTT method using the previously obtained calibration curve. The numbers of living cells thus determined by these 2 methods were compared by assuming that the number of cells at the start of the experiment to be 100%. Both the results were in good correlation, and under the present experimental conditions, it could be confirmed that the MTT method can be used in place of the cell counting method. This result for the case of HT1030 cells is shown in FIG. 6.

Assuming that the amount of VEGF expressed and the number of living cells in the absence of the phosphorothioate form of oligodeoxyribonucleotide and Tfx™-50 were 100%, the ratio of VEGF expression and the living cell number in the presence of the phosphorothioate form of oligodeoxyribonucleotide were determined.

For correction, the former rate of VEGF expression was divided by the latter rate of living cell number and expressed as corrected rate of VEGF expression. Corrected rate of VEGF expression and the rate of living cell number a re shown in Table 2.

Example 3

Confirmation of Antisense Nucleic Acid Effect in A549 Cell System

The phosphorothioate form of oligodeoxyribonucleotides expected to have the antisense nucleic acid effect was used as the antisense nucleic acid compounds to examine their inhibitory effect on the expression of VEGF in a cultured cell system in the same manner as in Example 2. That is, this experiment was carried out in a cell culture system using human lung cancer-derived A549 cells under sterilized conditions according to the reported method (M. Y. Chiang et al., The Journal of Biological Chemistry, Vol. 266, No. 27, pp. 18162–18172 (1991)), as follows:

A549 cells were placed in a 48-well plate and incubated at 37° C. in DMEM medium containing 10% fetal bovine serum in a 5% $CO_2$ atmosphere until they attained a 60 to 80% confluent state. After removal of the medium, the plate was washed with Opti-MEM medium (GIBCO-BRL). Tfx™-50 reagent (Promega) was put at a final concentration of 18 μg/ml to Opti-MEM medium containing 2.3 μM phosphorothioate form of oligodeoxyribonucleotide, and the mixture was stirred. After the mixture was left for 15 to 20 minutes at room temperature, 0.2 ml was put to each well, and the pate was incubated at 37° C. for 2 hours in a 5% $CO_2$ atmosphere. This solution was removed, and the plate was washed with DMEM medium containing 10% fetal bovine serum. Then, 100 μl DMEM medium containing 10% fetal bovine serum was put to each well and the plate was incubated at 37° C. for 3 hours in a 5% $CO_2$ atmosphere.

Corrected VEGF expression rate and rate of living cell number of A549 are shown in Table 2, along with the results for HT1080 cells.

TABLE 2

VEGF expression rate in HT1080 and A549 cells

| Sample # | HT1080 Corrected rate of VEGF expression (%) | HT1080 Rate of living cells obtained by the MTT method (%) | A549 Corrected rate of VEGF expression (%) | A549 Rate of living cells obtained by the MTT method (%) |
|---|---|---|---|---|
| U0370TS | 16 ± 1 | 84 ± 1 | 30 ± 4 | 90 ± 2 |
| U0393TS | 30 ± 2 | 84 ± 2 | 26 ± 1 | 98 ± 3 |
| U0397TS | 25 ± 3 | 82 ± 1 | 26 ± 1 | 96 ± 9 |
| U0401TS | 18 ± 2 | 83 ± 2 | 22 ± 1 | 95 ± 4 |
| U0406TS | 16 ± 1 | 83 ± 1 | 16 ± 1 | 87 ± 2 |
| RU0406TS | 66 ± 3 | 80 ± 2 | 67 ± 0 | 84 ± 7 |
| U0411TS | 13 ± 1 | 81 ± 2 | 27 ± 1 | 98 ± 2 |
| U0413TS | 12 ± 1 | 78 ± 0 | 26 ± 1 | 93 ± 3 |
| RU0413TS | 56 ± 2 | 81 ± 2 | 67 ± 0 | 83 ± 3 |
| U0416TS | 18 ± 1 | 81 ± 2 | 27 ± 1 | 91 ± 2 |
| U0420TS | 18 ± 1 | 85 ± 4 | 20 ± 3 | 91 ± 2 |
| U0424TS | 14 ± 1 | 85 ± 2 | 19 ± 1 | 93 ± 3 |
| U0843TS | 14 ± 1 | 84 ± 2 | 17 ± 1 | 79 ± 3 |
| U0848TS | 16 ± 2 | 85 ± 2 | 13 ± 1 | 82 ± 5 |
| U0853TS | 16 ± 1 | 85 ± 2 | 12 ± 1 | 81 ± 1 |
| U0857TS | 10 ± 0 | 81 ± 2 | 12 ± 1 | 85 ± 3 |
| U0860TS | 9 ± 1 | 85 ± 2 | 12 ± 1 | 87 ± 5 |
| U0865TS | 15 ± 1 | 86 ± 2 | 11 ± 1 | 87 ± 3 |

As is evident from Table 2, the relative errors of the corrected rate of VEGF expression were usually within 8% (15% even at the maximum) and thus there was little dispersion. Further, rate of living cells were about 80% or more (with the relative errors usually within about 6% and 9% even at the maximum), and there was no particular strong toxicity, and the amount of VEGF expressed by adding the phosphorothioate form of oligodeoxyribonucleotide as the antisense nucleic acid was apparently lower than that by adding the randomly sequenced phosphorothioate form of oligodeoxyribonucleotide.

Table 2 shows "expression rate (%)" where a lower value indicates a higher inhibitory effect of the antisense nucleic acid compound on expression of VEGF. The amount of VEGF expressed in the presence of phosphorothioate form of oligodeoxyribonucleotide as the antisense nucleic acid was apparently lower than the amount of VEGF expressed in the presence of the randomly sequenced phosphorothioate form of oligodeoxyribonucleotide. That is, in Table 2, any antisense compounds given "U" before numbers in "Sample #" in Table 1 brought about 30% or less expression rates which were lower than those by RU0406TS and RU0413TS used as control nucleic acid compounds, and almost all antisense compounds gave 20% or less, and some gave 10% or less. It is considered that these antisense compounds evidently inhibit expression of VEGF effectively.

It is apparent that the inhibitory effect of the antisense nucleic acid compound toward regions upstream of the translation region on expression of VEGF is superior to the inhibitory effect (54 to 70% expression) of the antisense nucleic acid compound toward the translation region itself on expression of VEGF.

As shown in Table 2, it was found that 9 oligodeoxyribonucleotides U0393TS to U0424T which were 2 to 5-nucleotides apart from each other and 6 oligodeoxyribonucleotides U0843TS to U0865TS which were 3 to 5-nucleotides apart from each other had an extremely strong inhibitory effect (30% or less expression). That is, antisense nucleic acid compounds toward regions at the 331- to 381-positions or thereabout and the 781- to 822-positions or thereabout in SEQ ID NO:1 have an extremely strong inhibitory effect on the production of VEGF (30% or less expression in any cells of A549 and HT1080 cells). The sequences from the 331- to 381-positions and from the 781- to 822-positions in SEQ ID NO:1 are hereinafter referred to as "region 1" and "region 2", respectively.

Table 2 shows the experimentally determined amounts of expressed VEGF where 9 kinds of 20-mer antisense nucleic acids which are complementary sequences to region 1, and located 2 to 5-nucleotides apart from each other. It can be easily estimated that antisense nucleic acids toward partial sequences in region 1 also exert an extremely strong inhibitory effect on production of VEGF, and the same effect can also be estimated with respect to region 2.

From the foregoing, it was found that expression of VEGF in human fibrosarcoma HT1080 cells and human cancer-derived A549 cells can be inhibited by phosphorothioate form of oligodeoxyribonucleotides having complementary nucleotide sequences to the selected nucleotide sequences or regions.

The present inventors revealed that antisense nucleic acid compounds complementary to 10 or more nucleotides generally inhibit expression of their target protein (WO 96/00286), and antisense nucleic acids continuously complementary to 10 or more nucleotides, preferably 13 or more nucleotides upstream of a translation region of a target protein exert a strong inhibitory effect on the target protein.

From these results, it can be presumed that regions in SEQ ID NO:1 which are preferable as the target of the antisense nucleic acid are as follows: a nucleotide sequence consisting of nucleotides 331 to 381 in SEQ ID NO:1 (SEQ ID NO:2), a nucleotide sequence consisting of nucleotides 781 to 822 in SEQ ID NO:1 (SEQ ID NO:3), a nucleotide sequence consisting of nucleotides 308 to 327 in SEQ ID NO:1 (SEQ ID NO:4), a nucleotide sequence consisting of nucleotides 331 to 350 in SEQ ID NO:1 (SEQ ID NO:5), a nucleotide sequence consisting of nucleotides 335 to 354 in SEQ ID NO:1 (SEQ ID NO:6), a nucleotide sequence consisting of nucleotides 339 to 358 in SEQ ID NO:1 (SEQ ID NO:7), a nucleotide sequence consisting of nucleotides 344 to 363 in SEQ ID NO:1 (SEQ ID NO:8), a nucleotide sequence consisting of nucleotides 349 to 368 in SEQ ID NO:1 (SEQ ID NO:9), a nucleotide sequence consisting of nucleotides 351 to 370 in SEQ ID NO:1 (SEQ ID NO:10), a nucleotide sequence consisting of nucleotides 354 to 373 in SEQ ID NO:1 (SEQ ID NO:11), a nucleotide sequence consisting of nucleotides 358 to 377 in SEQ ID NO:1 (SEQ ID NO:12), a nucleotide sequence consisting of nucleotides 362 to 381 in SEQ ID NO:1 (SEQ ID NO:13), a nucleotide sequence consisting of nucleotides 781 to 800 in SEQ ID NO:1 (SEQ ID NO:14), a nucleotide sequence consisting of nucleotides 786 to 805 in SEQ ID NO:1 (SEQ ID NO:15), a nucleotide sequence consisting of nucleotides 791 to 810 in SEQ ID NO:1 (SEQ ID NO:16), a nucleotide sequence consisting of nucleotides 795 to 814 in SEQ ID NO:1 (SEQ ID NO:17), a nucleotide sequence consisting of nucleotides 798 to 817 in SEQ ID NO:1 (SEQ ID NO:18), and a nucleotide sequence consisting of nucleotides 803 to 822 in SEQ ID NO:1 (SEQ ID NO:19). It can be easily presumed that an antisense nucleic acid compound which is continuously complementary to 10 or more contiguous nucleotides, preferably 13 or more nucleotides, more preferably 20 or more nucleotides in these nucleotide sequences, exerts a strong inhibitory effect on expression of its target protein VEGF.

In view of the role of VEGF as a tumor angiogenic factor in vivo (K. J. Kim et al., Nature, Vol. 362, April 29 issue, pp. 841–844 (1993); and S. Kondo et al., Biochemical and Biophysical Research Communications, Vol. 194, No. 3, pp. 1234–1241 (1993)), an antisense nucleic acid compound having 10 or more nucleotides, preferably 13 or more nucleotides, more preferably 20 or more nucleotides for SEQ ID NOS:2 to 19 is useful as a therapeutic agent such as anticancer drug to inhibit the growth of solid tumor cells or as a diagnostic agent for cancers.

What is claimed is:

1. An antisense nucleic acid compound having a sequence complementary to a sequence located 5' of a coding sequence for vascular endothelial growth factor which inhibits 50% or more of the expression of vascular endothelial growth factor in cells, wherein said sequence located 5' of the coding sequence for vascular endothelial growth factor has a sequence set forth in SEQ ID NOs:2 or 3.

2. The antisense nucleic acid compound according to claim 1 which inhibits 70% or more of the expression of vascular endothelial growth factor.

3. The antisense nucleic acid compound according to claim 1 which inhibits 80% or more of the expression of vascular endothelial growth factor.

4. The antisense nucleic acid compound according to any of claims 1 to 3 wherein said complementary sequence has at least 10 nucleotides.

5. The antisense nucleic acid compound according to any of claims 1 to 3 wherein said complementary sequence has 10 to 30 nucleotides.

6. The antisense nucleic acid compound according to claim 1, wherein said antisense is a phosphorothioate form.

7. A therapeutic agent comprising the antisense nucleic acid compound of claim 1 as an active ingredient.

8. A diagnostic agent comprising the antisense nucleic acid compound of claim 1 as an active ingredient.

9. An antisense nucleic acid compound having a sequence complementary to any of SEQ ID NOs:4 to 19.

10. The antisense nucleic acid compound according to claim 9 which inhibits 70% or more of the expression of vascular endothelial growth factor.

11. The antisense nucleic acid compound according to claim 9 which inhibits 80% more of the expression of vascular endothelial growth factor.

12. The antisense nucleic acid compound according to any one of claims 9, 10 or 11 wherein said complementary sequence has at least 10 nucleotides.

13. An antisense nucleic acid compound having a sequence substantially complementary to any of SEQ ID NOs:2 or 3 and which inhibits 50% or more of the expression of vascular endothelial growth factor in cells.

14. The antisense nucleic acid compound according to claim 13 which inhibits 70% or more of the expression of vascular endothelial growth factor.

15. The antisense nucleic acid compound according to claim 13 which inhibits 80% or more of the expression of vascular endothelial growth factor.

16. The antisense nucleic acid compound according to claim 13 which has a nucleotide sequence complementary to at least 10 contiguous nucleotides of any of SEQ ID NOs:2 or 3.

17. The antisense nucleic acid compound according to claim 13 which comprises a sequence of 10 to 30 nucleotides.

* * * * *

SEQUENCE LISTING

<160> NUMBER OF SEQ ID NOS: 21

<210> SEQ ID NO 1
<211> LENGTH: 1038
<212> TYPE: DNA
<213> ORGANISM: Homo sapiens

<400> SEQUENCE: 1
tcgcggaggc ttggggcagc cgggtagctc ggaggtcgtg gcgctggggg ctagcaccag     60
cgctctgtcg ggaggcgcag cggttaggtg gaccggtcag cggactcacc ggccagggcg    120
ctcggtgctg gaatttgata ttcattgatc cgggttttat ccctcttctt ttttcttaaa    180 cattttttt taaaactgta ttgtttctcg ttttaattta tttttgcttg ccattcccca    240
cttgaatcgg gccgacggct tggggagatt gctctacttc cccaaatcac tgtggatttt    300
ggaaaccagc agaaagagga aagagtagc aagagctcca gagagaagtc gaggaagaga    360
gagacggggt cagagagagc gcgcgggcgt gcgagcagcg aaagcgacag gggcaaagtg    420
agtgacctgc ttttgggggt gaccgccgga gcgcggcgtg agccctcccc cttgggatcc    480
cgcagctgac cagtcgcgct gacggacaga cagacagaca ccgcccccag ccccagctac    540
cacctcctcc ccggccggcg gcggacagtg gacgcggcgg cgagccgcgg gcaggggccg    600
gagcccgcgc ccggaggcgg ggtggagggg gtcggggctc gcggcgtcgc actgaaactt    660
ttcgtccaac ttctgggctg ttctcgcttc ggaggagccg tggtccgcgc ggggggaagcc    720 gagccgagcg gagccgcgag aagtgctagc tcgggccggg aggagccgca gccggaggag    780
ggggaggagg aagaagagaa ggaagaggag aggggccgc agtggcgact cggcgctcgg    840
aagccgggct catggacggg tgaggcggcg gtgtgcgcag acagtgctcc agccgcgcgc    900
gctccccagg ccctggcccg ggcctcgggc cggggaggaa gagtagctcg ccgaggcgcc    960
gaggagagcg ggccgcccca cagcccgagc cggagaggga gcgcgagccg cgccggcccc   1020
ggtcgggcct ccgaaacc                                                  1038

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence: Artificial nucleic acid sequence

<400> SEQUENCE: 2
aagagctcca gagagaagtc gaggaagaga gagacggggt cagagagagc g          51

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 3
ggggaggagg aagaagagaa ggaagaggag aggggccgc ag                     42

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 4
agcagaaaga ggaaagaggt                                             20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 5
aagagctcca gagagaagtc                                             20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 6
gctccagaga gaagtcgagg                                             20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 7
cagagagaag tcgaggaaga                                             20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence -continued

<400> SEQUENCE: 8
agaagtcgag gaagagagag                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 9
tcgaggaaga gagagacggg                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 10
gaggaagaga gagacggggt                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 11
gaagagagag acggggtcag                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 12
agagagacgg ggtcagagag                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 13
agacggggtc agagagagcg                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence -continued

```
<400> SEQUENCE: 14 gggaggagg aagaagagaa                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 15
ggaggaagaa gagaaggaag                                                  20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 16
aagaagagaa ggaagaggag                                                  20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 17
agagaaggaa gaggagaggg                                                  20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 18
gaaggaagag gagaggggc                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 19
aagaggagag ggggccgcag                                                  20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 20
```

```
ttccttccct tctagtcctc                                                    20
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Artificial
      nucleic acid sequence

<400> SEQUENCE: 21

```
ccctctcgtc tcctactctc                                                    20
```